(12) United States Patent
Schreiber et al.

(10) Patent No.: US 6,333,991 B1
(45) Date of Patent: Dec. 25, 2001

(54) ANALYSIS OF RADIOGRAPHIC IMAGES

(75) Inventors: Bernd Schreiber, Hamburg; Frank Kreuder, Krefeld, both of (DE)

(73) Assignee: Elekta AB, Stockholm (SE)

(*) Notice: Subject to any disclaimer, the term of this patent is extended or adjusted under 35 U.S.C. 154(b) by 0 days.

(21) Appl. No.: 09/190,311

(22) Filed: Nov. 12, 1998

(30) Foreign Application Priority Data

Nov. 15, 1997 (GB) .................................................. 9724110

(51) Int. Cl.⁷ ...................................................... G06K 9/00
(52) U.S. Cl. ............................................................ 382/132
(58) Field of Search .................................... 382/128, 130, 382/131, 132, 172, 194, 260, 263, 264, 273, 284, 289, 293, 295, 296, 298; 345/437, 438, 439

(56) References Cited

U.S. PATENT DOCUMENTS

| | | | |
|---|---|---|---|
| 4,323,973 | 4/1982 | Greenfield | 382/130 |
| 4,335,427 | 6/1982 | Hunt | 600/407 |
| 4,731,863 | * 3/1988 | Sezan et al. | 382/172 |
| 5,253,169 | * 10/1993 | Corby, Jr. | 600/431 |
| 5,274,551 | * 12/1993 | Corby, Jr. | 600/433 |
| 5,295,200 | * 3/1994 | Boyer | 382/280 |
| 5,452,367 | * 9/1995 | Bick et al. | 382/128 |
| 5,805,663 | * 9/1998 | Mihara | 378/98.2 |
| 6,038,281 | * 3/2000 | Mazess | 378/54 |

FOREIGN PATENT DOCUMENTS

| | | | |
|---|---|---|---|
| 0 331 274 | 9/1989 | (EP) | G06F/15/20 |
| 0 362 849 | 4/1990 | (EP) | G06F/15/68 |
| 0 744 157 | 11/1996 | (EP) | A61B/6/00 |
| WO98/02091 | 1/1998 | (WO) | G06T/7/00 |
| WO98/19272 | 5/1998 | (WO) | A61B/5/05 |

* cited by examiner

*Primary Examiner*—Andrew W. Johns
*Assistant Examiner*—Shervin Nakhjavan
(74) *Attorney, Agent, or Firm*—Kinney & Lange, P.A.

(57) ABSTRACT

Two analysis methods for a portal image are disclosed, one to check apparatus setup and the other to check patient positioning. The first involves preparing a reference radiation field image and a sample radiation field image from a reference image and a sample image respectively by, in order, (i) defining a threshold value and (ii) setting pixels within the respective images to a dark or a bright state if darker or brighter than the threshold value, (optionally) comparing the reference radiation field image and the sample radiation field image to determine at least one of their relative rotation, translation and scaling, subtracting one of the radiation field images from the other thereby to obtain a difference image, and inspecting the difference image to ascertain changes in the radiation field between preparation of the reference image and the sample image. The second comprising the steps of filtering at least the sample image to remove low frequency variations, selecting a region of interest (ROI) within the reference and sample images, correlating the ROI of the reference image with the ROI of the sample image, and determining the relative displacements of the reference image and the sample image.

29 Claims, 11 Drawing Sheets

ANALYSIS OF RADIOGRAPHIC IMAGES

TECHNICAL FIELD OF THE INVENTION

The present invention relates to the analysis of radiographic images.

BACKGROUND ART

Linear accelerators have been in use for a significant time for the treatment of severe medical conditions such as cancer. The principle of operation of these devices is essentially that electromagnetic radiation of sufficiently high energy (greater than 1 MeV) causes the death and/or destruction of living cells in its path. If therefore a beam of high energy photons or electrons is directed to a cancerous area, the cancer will be destroyed.

It is clear that this treatment has the potential to cause harm to the patient if the radiation is incident on healthy tissue. It is therefore common practice to collimate the beam in order to limit its spatial extent and therefore limit the amount of tissue, healthy or otherwise, upon which it is incident. Collimators to this effect are known, and include collimators of variable size and shape which are capable of selectively blocking the radiation beam at its edges thereby to produce a beam whose shape corresponds to that of the tumour.

In this situation, it is clearly necessary to ensure that the positioning of the patient is accurate. This is generally done by shining one or more collimated light sources on the patient, such as low energy lasers. When the patient is first treated, ink marks are placed on the patient's skin and these are subsequently used to align the patient relative to the lasers. This is able to provide a positioning accuracy of approximately 2–5 mm.

As a result, the shaped radiation beam needs to be formed to the approximate outline shape of the tumour plus a margin in each direction to allow for positioning error. This results in a significant volume of tissue around the tumour which is needlessly irradiated. If the patient could be positioned more accurately beneath the beam, then this margin around the tumour could be reduced thereby limiting the damage caused to the patient's healthy tissue.

It is known to prepare a "Portal image" derived from the radiation transmitted through the patient and incident on a photographic plate or other detector. However, the absorption co-efficients of bone, tissue etc. at the energies normally used for radiotherapy are very similar and therefore a Portal image shows very little detail.

SUMMARY OF THE INVENTION

The present invention provides a method of electronically analysing the Portal image which is able to distil from the initially indistinct image information which is relevant to the treatment and to the positioning of the patient. In its first general stage, the method of the present invention determines whether or not the radiation beam is correctly set up. In its second general stage, the present invention determines whether or not the patient is positioned correctly in the radiation beam. Clearly, in any practical use of the invention, it will be preferred that both stages are employed. The description of this Application should therefore be read accordingly. However, the Application relates to the two analysis stages independently and the following summary of the invention should likewise be read accordingly.

In its first general stage, therefore, the present invention relates to a method of analysing a radiographic image comprising the following steps;

(a) preparing a reference image;
(b) preparing a sample image;
(c) preparing a reference radiation field image and a sample radiation field image from the reference image and the sample image respectively by, in order, (i) defining a threshold value and (ii) setting pixels within the respective images to a dark or a bright state if darker or brighter than the threshold value;
(d) optionally, comparing the reference radiation field image and the sample radiation field image to determine at least one of their relative rotation, translation and scaling;
(e) subtracting one of the radiation field images from the other thereby to obtain a difference image;
(f) inspecting the difference image to ascertain changes in the radiation field between preparation of the reference image and the sample image.

This method therefore provides a first warning as to whether the radiation fields are appropriate. It may generate an abnormal result if, for example, the collimator is incorrectly set.

Step (d) would be unnecessary if, for example, the image capture apparatus was normally stable enough to preclude all rotation, translation or scaling.

The threshold value is preferably calculated by determining the pixel grey scale histogram of one or both images and selecting a value between two peaks of the histogram. The value is preferably approximately half-way between the peaks, for example within 10% of the mid-point.

The dark state is preferably a zero brightness, and the bright state is preferably a maximum brightness, for example 1.

A suitable method of inspecting the difference image is by counting the total number of pixels in either the dark or the bright state. If this total number is above a preset threshold, or less than a preset threshold if the pixel type being counted is the predominant pixel within the image, then this can be considered an error value.

It is preferred if an alarm is generated if inspection shows a significant difference between the images. The difference can be measured as greater or less than a preset number or percentage of the total number of pixels. This preset number can be fixed by the system or set in accordance with the practice and technique of an individual hospital.

It is to be expected that the difference image will contain a line of single pixels at the boundary of the field, due to limitations in the calculation. This can be removed by a suitable filter, if desired. The remaining difference pixels will correspond to an area of field mismatch which can be compared to the preset number.

In its second general stage, the present invention proposes a method of distilling from the Portal images sufficient information regarding the patient's internal structure to allow determination of the patient positioning within the radiation field.

The present invention therefore provides, in its second general stage, a method of analysing a radiographic image comprising the following steps:

(a) preparing a reference image;
(b) preparing a sample image;
(c) filtering at least the sample image to remove low frequency variations;
(d) selecting a region of interest (ROI) within the reference and sample images;
(e) correlating the ROI of the reference image with the ROI of the sample image;

(f) determining the relative displacements of the reference image and the sample image.

The region of interest (ROI) may be a selected field of the image. Alternatively, it can be the entire image, although it is particularly preferred if the edge of the image is avoided. This is because the edge generally includes details of the radiation field edge, which tends to be either very bright or very dark. Thus, such areas of the image tend to predominate in the correlation step. It is therefore preferred if a border is eliminated by the steps of shrinking the radiation field image generated in the first general stage. This shrunken image can, optionally, be thresholded and multiplied with the sample and/or reference image of the second general stage. Shrinking a bit map image can easily be carried out by setting the pixel to a dark state unless all four neighbours are bright. To shrink an image by more than one pixel, the process can either be repeated, or can be carried out by examining pixels a set distance away in each direction. In the present invention, it is preferred if that distance is between 15 and 30 pixels.

It is naturally preferred if this aspect of the invention is carried out in combination with the first aspect, and the output result of this aspect is the calculated difference between the radiation field displacement and the image displacement. This will reveal the displacement of the patient relative to the radiation field, which is of course the value of interest. As noted above, it may be that certain radiation generators are sufficiently stable to ensure that the imaged radiation field does not move.

According to the present invention, the reference image can be either a Portal image from the first treatment, or a pre-treatment test image, or a digitally reconstructed radiograph.

The sample image can be a Portal image taken during a radiotherapy treatment.

It is particularly preferred if the sample image is captured electronically and analysed during the therapeutic radiotherapy treatment. Such treatments usually last one minute or two minutes, and sufficient data is usually available to produce a sample image within up to 15 seconds. It is preferred if data is captured during the first 10 seconds or less, particularly preferred if it is captured during the first 5 seconds or less.

It would be advisable to end the radiotherapy session if inspection according to either stage reveals a significant error. This will allow the patient to be repositioned more accurately, preventing unnecessary irradiation of healthy tissue.

The present invention also relates to a radiotherapy treatment apparatus comprising means for digitally capturing a Portal image and means for analysis of that image, adapted to carry out the steps of any image analysis method set out above.

The present invention also relates to a method of treating a patient by radiotherapy, comprising the steps of placing the patient in range of a radiation source, activating the source, capturing a sample Portal image and analysing the sample image according to any image analysis method set out above, and de-activating the radiation source if analysis shows a significant difference between the images.

BRIEF DESCRIPTION OF DRAWINGS

An embodiment of the present invention will now be described by way of example, with reference to the accompanying Figures; in which.

DETAILED DESCRIPTION OF THE INVENTION

An analysis method according to the present invention will now be described. The method is divided into the following steps:

1. Elimination of detector-related point errors in the Portal image.
2. Segmentation of the radiation field and calculation of the relative translation, rotation and scaling of the radiation fields including verification of geometrical similarity.
3. Automatic Contrast Enhancement
4. Noise suppression by a Gaussian filter.
5. Elimination of the slowly varying grey-levels.
6. Elimination of the border of the radiation field.
7. Determination of the translation and rotation of the anatomy by calculating the correlation between the two pre-processed images with or without an ROI.

Figure 8:
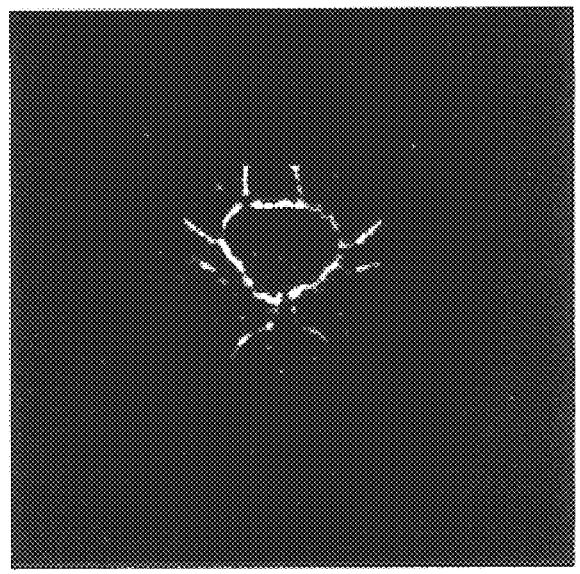
FIG. 8 shows the image of FIG. 7 after inversion.

In this discussion, the reference image is a Portal image derived during the first treatment session. It is however possible according to the invention to replace this image with a digitally reconstructed radiograph as illustrated in FIG. 8. Such radiographs are known per se, together with method support their construction. The principle of the invention is the same regardless of which type of images used to create the reference image, and therefore no further discussion will be given. Other reference images can be used, such as a diagnostic X-ray image from a treatment simulation, or a hard drawing of bone structures of the patient. A DRR or X-ray image has the advantage of a higher contrast as compared to a Portal image.

1. Elimination of Point Errors

Portal images contain both noise and point errors, ie very dark or very bright pixels with grey-levels which are markedly different compared with their neighbours. These arise when the camera receives a direct hit from a scattered MeV photon. They are not therefore an informative part of the image. Such errors should ideally be eliminated, although this step may not be necessary depending on the quality of the image capture apparatus. A Gaussian filter will not eliminate such an error as it serves only to reduce the peak height of a point error and smear the error out amongst neighbouring pixels. Other linear filters generally have a similar effect. Elimination of point errors can in general only be achieved with a non-linear filter such as a median filter. A 3×3 median filter will in the present case achieve the desired result. In a 3×3 median filter, the value of the centre pixel is replaced with the median value of its eight neighbours. Thus, individual point errors are eliminated completely with little effect on other types of grey-level variation.

2. Segmentation and Matching of the Radiation Field

Figure 1:
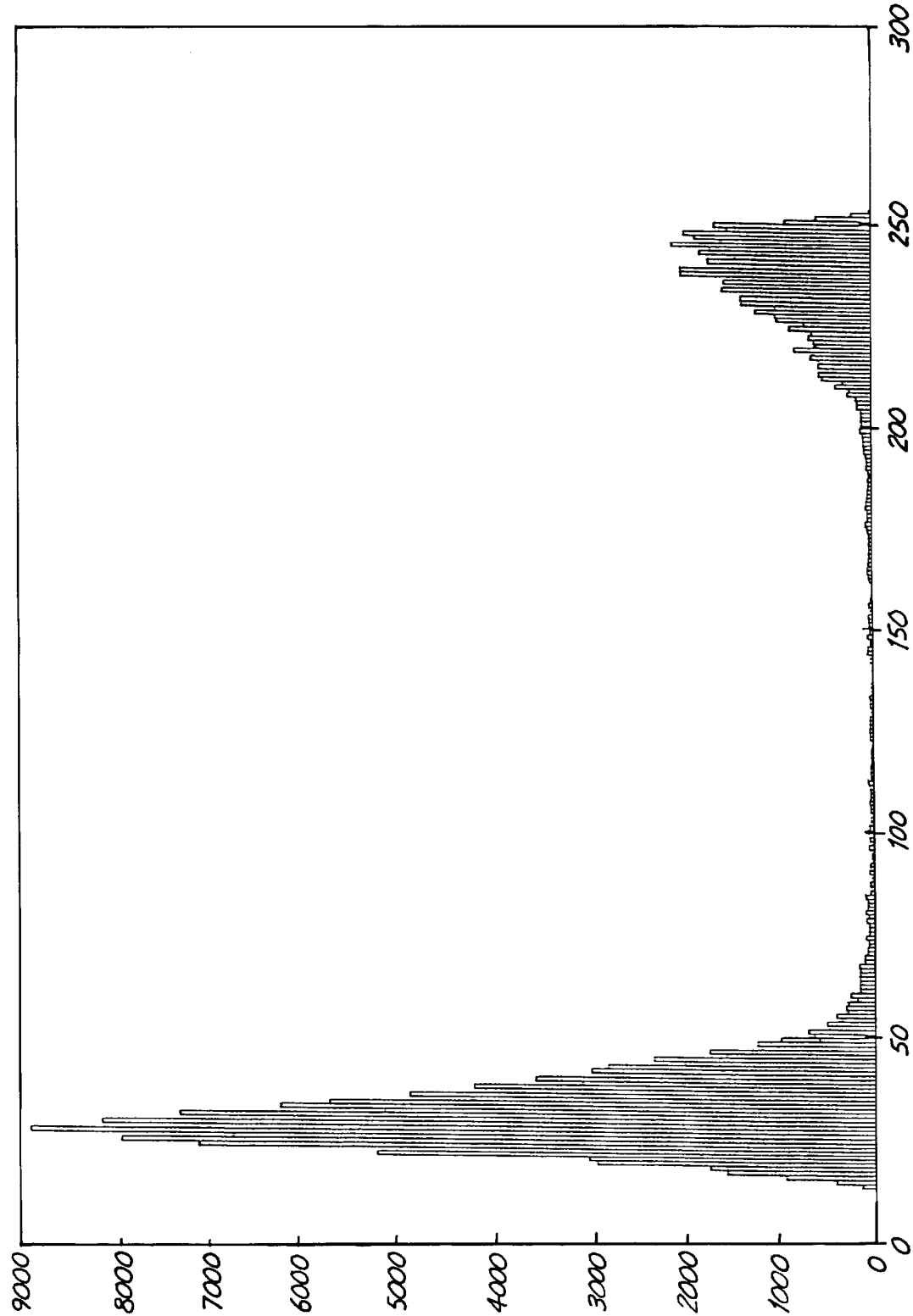
FIG. 1 shows a histogram of a typical Portal image.

The histograms of the two median filtered grey-level images from Section 1 are calculated. In the case of Portal images, the histogram will generally be bimodal, one maximum belonging to the radiation field and the other belonging to the part of the image which lies in the shadow of the collimator. A typical histogram is shown at FIG. 1. The mean position between the two maxima is used as a threshold for segmentation of the radiation field. Thus, each pixel is essentially thresholded according to whether its individual grey-level is above or below the threshold. This generates a binary image of the radiation field in which grey-levels are either 1 or 0. Thus, the binary image b(i,j) of the radiation field is calculated by setting pixels with a grey-level f(i,j) larger than the threshold to 1 and pixels with a grey-level f(i,j) smaller than the threshold to 0;

$$b(i, j) = \begin{cases} 1, & \text{if } f(i, j) \geq \text{Threshold} \\ 0, & \text{if } f(i, j) < \text{Threshold} \end{cases}$$

Figure 2:
FIG. 2 shows an image after thresholding.

Such a binary image is illustrated at FIG. 2, and essentially shows the collimator shape.

After this has been done to both the sample and the reference image, the relative translation, rotation and scaling of two radiation fields is determined straightforwardly by calculating the moments of their binary images. The first order moments of the binary image b(i,j) deliver the centre of gravity (x,y) of the radiation field:

$$\bar{x} = \frac{\sum_{i,j} i \cdot b(i, j)}{\sum_{i,j} b(i, j)} \quad \text{and} \quad \bar{y} = \frac{\sum_{i,j} j \cdot b(i, j)}{\sum_{i,j} b(i, j)}$$

The orientation and size of the radiation field can be inferred from the second order moment matrix $M_{kl}$ which is defined as follows:

$$M_{kl} = \frac{\sum_{i,j} (i - \bar{x})^k \cdot (j - \bar{y})^l \cdot b(i, j)}{\sum_{i,j} b(i, j)} \quad \text{with}$$

$k, l = 0, 1, 2$ and $k + l = 2$

The matrix $$\begin{pmatrix} M_{02} & M_{11} \\ M_{11} & M_{20} \end{pmatrix}$$

is diagonalized and its eigenvalues and corresponding eigenvectors are determined. One gets for the larger eigenvalue $$\lambda = \frac{M_{20} + M_{02} + \sqrt{(M_{20} - M_{02})^2 + 4 \cdot M_{11}^2}}{2}$$

The angle θ of its eigenvector with the x-axis is:

$$\theta = \arctan \frac{M_{02} - M_{20} + \sqrt{(M_{02} - M_{20})^2 + 4 \cdot M_{11}^2}}{2 \cdot M_{11}}$$

The relative translation (Δx,Δy), relative rotation Δθ and scaling σ of the radiation fields are then:

$$\Delta x = \bar{x}_{portal} - \bar{x}_{reference}, \Delta y = \bar{y}_{portal} - \bar{y}_{reference}$$

$$\Delta\Theta = \Theta_{portal} - \Theta_{reference}$$

$$\sigma = \sqrt{\frac{\lambda_{portal}}{\lambda_{reference}}}$$

Usually, large values for the relative translation, rotation and scaling indicated that the two radiation fields are of different shape whereas small values indicate that the radiation field has been chosen correctly. Nevertheless, a large value, e.g. for the translation does not necessarily mean that the radiation field is wrong.

Figure 3:
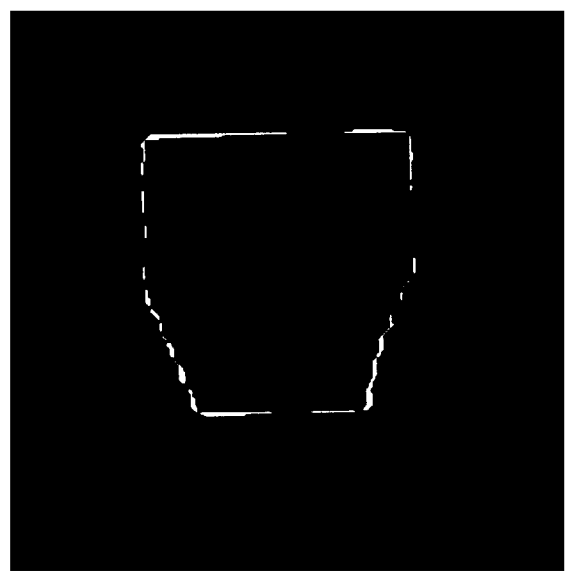
FIG. 3 shows a difference image.

To detect errors in the radiation field, one of the binary images is back transformed (inverse translation, inverse rotation and inverse scaling) and then subtracted from the other in order to verify the geometrical similarity of the two images. If both radiation fields are almost identical as applied to the patient then nearly all pixels of the difference image thus generated will be zero, as shown in FIG. 3. This last step is valuable because a simple translation of the radiation field will be meaningless, for example showing a translation of the camera between capturing the two images. This could, for example, be caused by removal and refitting of the camera between the two treatments. In that case a translation of the radiation field will be apparent despite the patient being in the correct position relative to the beam. However, demonstrating the geometric similarity of the collimated shapes demonstrates that the apparatus has been configured correctly and is applying the correct radiation field to the patient. Errors at this level are easily made but very significant in terms of patient outcome.

3. Automatic Contrast Enhancement

As mentioned above, the histogram of the median-filtered grey-level image has two peaks. The right peak (as shown in FIG. 1) contains the anatomical information. To enhance the anatomical structures of interest, an automatic contrast enhancement is performed: all grey-levels on the left side of that peak are set to zero, all grey-levels on the right side are set to 255 and in between a linear grey-level transformation is applied. The result is an image where bony structures are much more visible to a human observer.

4. Noise Suppression

A Gaussian filter is applied for noise suppression of the grey-level images demonstrated at Section 1. This leads to an improvement of the signal to noise ratio through the suppression of high frequencies, which usually constitute noise. Gaussian filters of the size between 7×7 and 15×15 pixels generally give good results.

5. Elimination of the Slowly Varying Grey-levels

This step is essentially a calculation of the rate of change of pixels, thereby eliminating slow variations. This step leads from a grey-level based correlation method to a structure based correlation method which gives substantially more robust results. If slowly varying grey-levels are allowed to remain in the image, these have a significant influence on the correlation. However, after processing the image from Section 4 above (FIG. 4) with a 15×15 block filter, an image is generated which contains only information regarding slowly varying grey-levels. If this image is subtracted from the image produced at Section 4 (FIG. 4), an image is produced where edges are relatively enhanced (FIG. 5) and slowly varying grey-levels are eliminated. This is in essence a high pass filter. Thus, in combination with Section 33, a high pass and a low pass filter are applied to the image. This order could clearly be reversed with little detrimental effect on the image.

It is of course the positions of the edges embedded in the image which is necessary for image registration; air bubbles are very distinct in non-structure based images and tend to influence correlation; by the above process they are reduced from an area-like structure to simply bare border lines which are then almost negligible in correlation. Thus, a matching is possible despite the presence of inevitable air bubbles.

Figure 6:
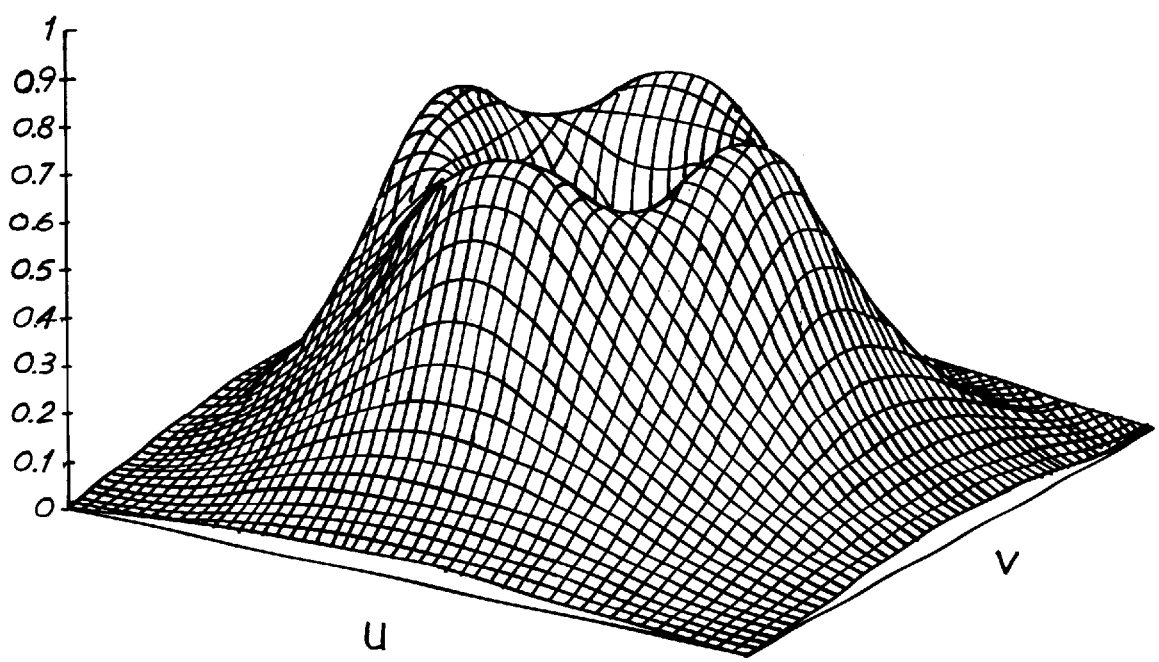
FIG. 6 illustrates the Bandpass filter of the present invention.

This can be achieved by convoluting the contrast enhanced images with a Bandpass filter to extract bony structures as much as possible. Noise reduction is done by the suppression of high frequencies. The suppression of low frequencies removes the slowly varying background intensities and reduces air bubbles from an area-like structure to their borderlines which are almost negligible in the correlation. The Bandpass filter is a combination of a blockfilter $b(x,y)$ filtering with a square of constant pixel values) and a Gaussian filter $g(x,y)$. The filtered image $p(x,y)$ is given by $$p(x,y)=g(x,y)*(I(x,y)-b(x,y))*f(x,y)$$

where the symbol * means convolution and $I(x,y)$ is the identity operation. After testing with hundreds of image pairs from different body regions, it was found that 15×15 convolution kernels for $b(x,y)$ and $g(x,y)$ are good choices for the Bandpass filter (since the pixel size of the Portal images we used is 0.5 mm, this results in a mean-frequency of roughly 0.3 $mm^{-1}$. Because of the relatively large kernel sizes the convolution was carried out in Fourier domain by a Fast Fourier Transformation (FFT). FIG. 6 illustrates the Bandpass filter.

6. Elimination of the Border

The elimination of the border from the image is easiest if the radiation field image (Section 2) is employed. This radiation field image can be shrunk by examining each point in the radiation field to determine whether any one neighbouring point with the distance a (ie (x+a,y), (x−a,y), (x,y+a), (x,y−a)) equals zero. If this is the case, the first point is set to zero in the mask image. If all four neighbours have the value 1, the point retains its original value. The result of this is a shrunken radiation field image, which after multiplication leads to the image in FIG. 5. This is essentially the same but without the border. This border, consisting of a prominent black and/or white area would otherwise contribute significantly to the correlation.

The distance A can be approximately 30 pixels when a 15×15 block filter is used, ie about twice the size of the block filter. Suitably, the ratio is between 0.5 and 3 times the size of the block filter.

7. Determination of the Translation and Rotation of the Anatomy

In a reference image from Section 6 (FIG. 8), one chooses a region of interest (ROI) which contains the anatomical structures of interest and does not contain artifacts. It is often possible to use the entire reference image for determination, but this is not necessary and in particular cases the skill of the radiographer can be deploy in selecting an ROI which gives the best correlation. A major advantage of the present invention is that reliable results are possible based on the entire image; this permits automatic of the comparison and to off-line matching. The similarity of the ROI with a shifted section of the second Portal image from Section 5 is determined by calculating the normalised cross correlation (NCC) as a suitable similarity measure. The maximum of the NCC thus determines the translation of the anatomy. A suitable method of calculating the NCC quickly is by the use of a Fast Fourier Transformation (FFT), for the simple reason that a correlation in the spatial domain corresponds to simple multiplication in the frequency domain.

After the relative translation has been calculated, the rotation of the patient on the treatment table can be determined. An FFT is particularly preferred at this stage as translation and rotation decouple in frequency space. The rotation can be determined by calculating two new images which contain the absolute values of the fully transformed images from Section 5. One of these images is then rotated within a prescribed range and the NCC calculated by correlating the rotated image with the second image. The maximum of the NCC then provides the rotation of the anatomy.

Figure 4:
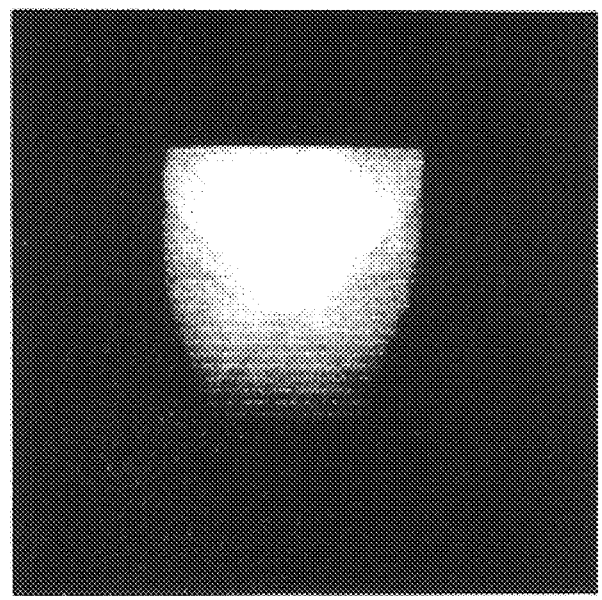
FIG. 4 shows a sample image after suppression of high frequency variations (noise)
Figure 5:
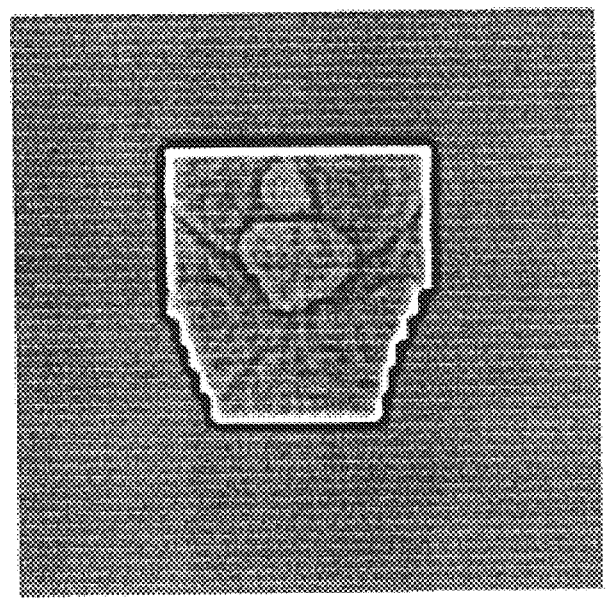
FIG. 5 shows the result of eliminating all but slowly varying grey-levels from FIG. 4.

FIG. 5 shows the Bandpass filtered image of FIG. 4. The Bandpass filter responds to radiation field edges as well as to bony details and additional processing (section 6 above) is added to remove the borderline of the radiation field (FIG. 8). Bony ridges are expressed as negative values of $p(x,y)$. For an additional enhancement positive pixel values are set to zero and negative pixel values are inverted to positive values (FIG. 8). The resulting image contains the position of bony ridges which is exactly the information necessary for image registration. Because of the elimination of the slowly varying grey-levels, the reduction of the air bubbles to their borderlines, and the removal of the field edge it is often possible to calculate the translation between the two images without choosing a RO1 in the Reference Image, thereby using as much image information as possible. As a measure of similarity the Normalized Cross Correlation is used. For a fast implementation the calculation is done in frequency domain by applying a Fast Fourier Transformation. The correlation function $c_N(a,b)$ is given by $$C_N(a,b) = \frac{FT^{-1}(FT^*(p_1(x,y)) \cdot FT(p_2(x,y)))}{\left(\sum_{x,y} p_1^2(x,y) \cdot \sum_{x,y} p_2^2(x,y)\right)^{\frac{1}{2}}}$$

where $p^1(x,y)$ and $p_2(x,y)$ are two Bandpass filtered Portal images FT and $FT^{-1}$ mean forward and backward Fourier transform, respectively, * means complex conjugation and the denominator is normalizing the correlation coefficient ($C_N$ is one for a perfect match of two identical images). The maximum of the correlation function represents the best match of the Reference Image with the Portal image and delivers thereby the translation (a,b) of the patient on the treatment table. By calculating the complete correlation function it is possible to detect even large translations of the patient reliably which are most important for interrupting the treatment. Another virtue of the Fourier based method is that one is able to find the global maximum of the correlation function safely. There is no danger to stay at local maxima as it is possible using maximum searches in spatial domain like hill-climbing or Downhill simplex-method [23]. By combining the translation of the patient (a,b) with the translation of the radiation field ($\Delta x, \Delta$) which has been calculated in II.2. one gets finally for the translation ($t_x, t_y$) of the patient relative to the radiation field:

$$t_x = a - \Delta, t_y = b - \Delta y$$

If this translation exceeds a threshold (for example 5 mm) the treatment is interrupted.

It will clearly be advisable to generate an alarm of some sort if the patient positioning error is above a certain preset threshold. For example, it could be an audible alarm or it could constitute an automatic deactivation of the radiation generator. Alternatively, a servo-controlled patient table could be provided such that after deactivation of the radiation field the patient can automatically be re-positioned according to the detected error. The entire process is then preferably repeated with a new sample image.

Figure 9:
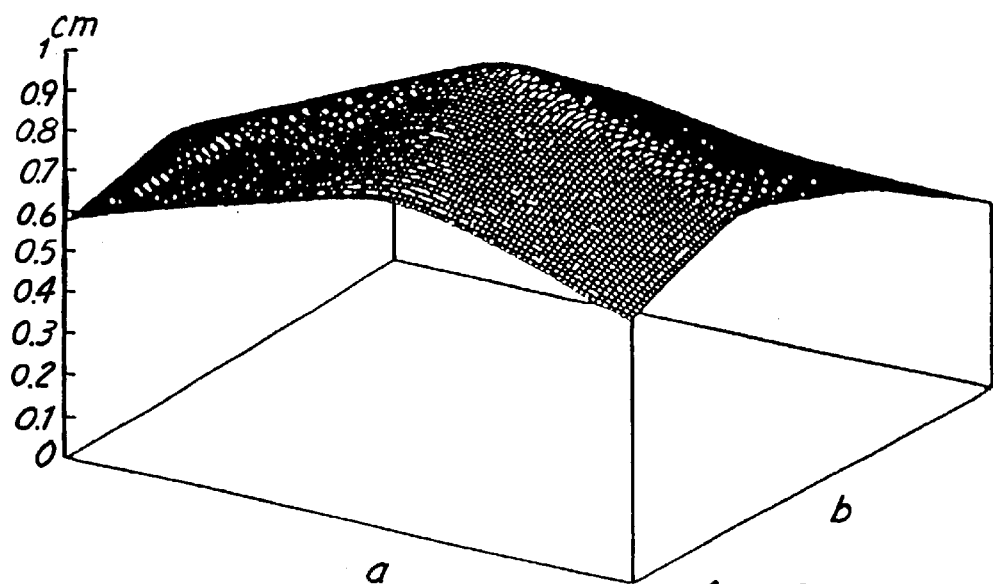
FIG. 9 shows the correlation co-efficient of two grey-level images prior to analysis according to the present invention.
Figure 10:
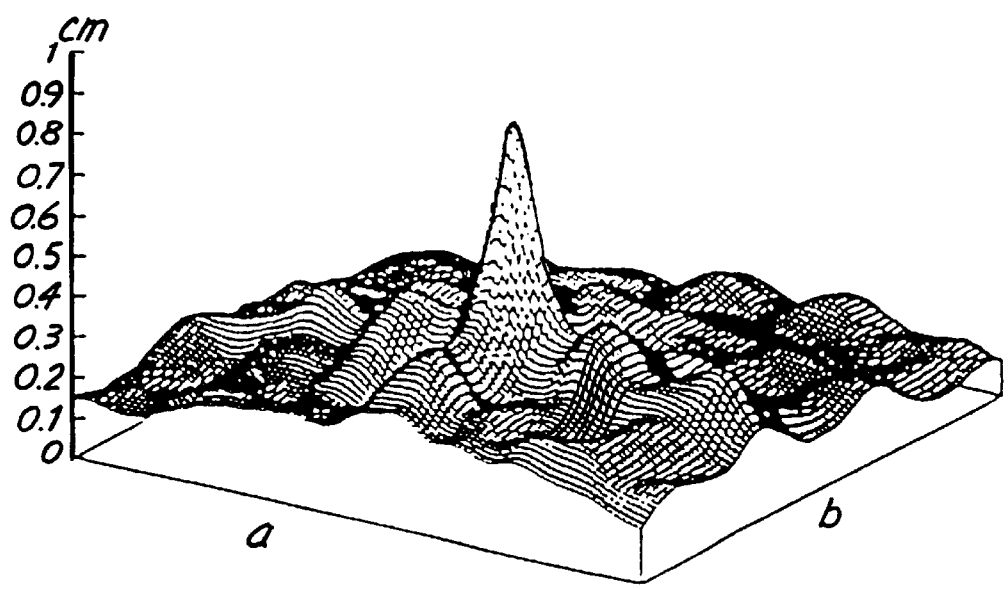
FIG. 10 shows the correlation co-efficient of two images after analysis according to the present invention.
Figure 11:
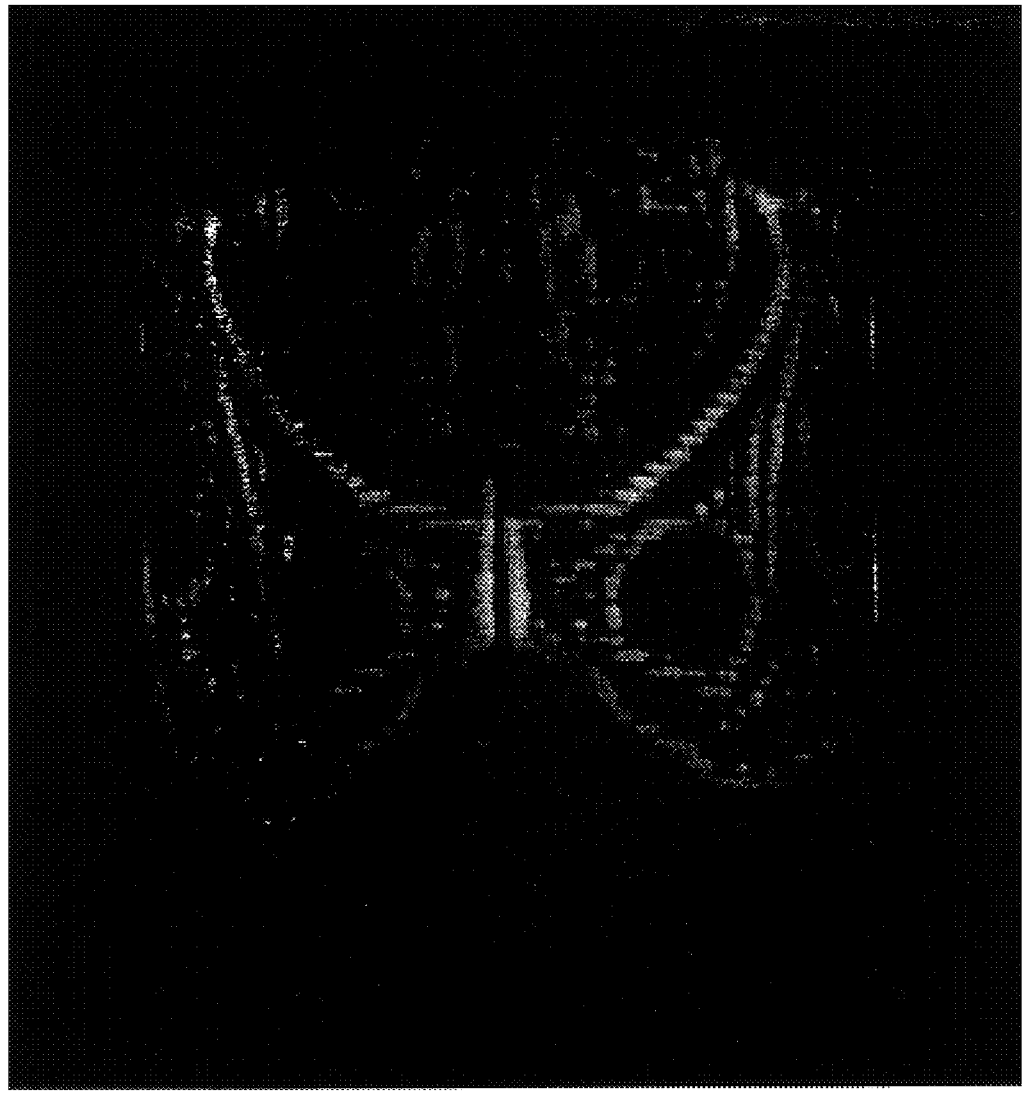
FIG. 11 shows a digitally reconstructed radiograph.

FIGS. 9 and 10 show the correlation coefficients of the two grey-level images before and after processing to reveal the internal structure. Thus, FIG. 9 shows the correlation coefficients of the bare grey-level images. It can be seen that whilst a clear maximum exists, the gradient to the maximum is relatively shallow meaning that the precise position of the maximum cannot be determined accurately. FIG. 10 on the other hand shows the correlation co-efficents of the two structure based images, and whilst there are many maxima in the image, one maxima stands out as being the clear best correlation. That maxima is sharply defined and it is a relatively simple matter to determine its position accurately.

RESULTS

The above described algorithm has been tested with Portal images received from the Department of Radiation Oncology at the William Beaumont University Hospital in Royal Oak, Mich., USA. 1139 pairs of Portal images of different anatomical regions (pelvis, lungs, head/neck region) were registered. The matching results are summarised in the following table:

| Anatomical Region | Pairs of Images | Successful Matching | Success Rate |
|---|---|---|---|
| Pelvis AP/PA | 544 | 536 | 99% |
| Pelvis lateral | 325 | 316 | 97% |
| Lungs | 144 | 137 | 95% |
| Head nasal | 51 | 51 | 100% |
| Head temporal | 39 | 39 | 100% |
| Auricular region | 36 | 33 | 92% |
| Total | 1139 | 1112 | 98% |

Figure 12:
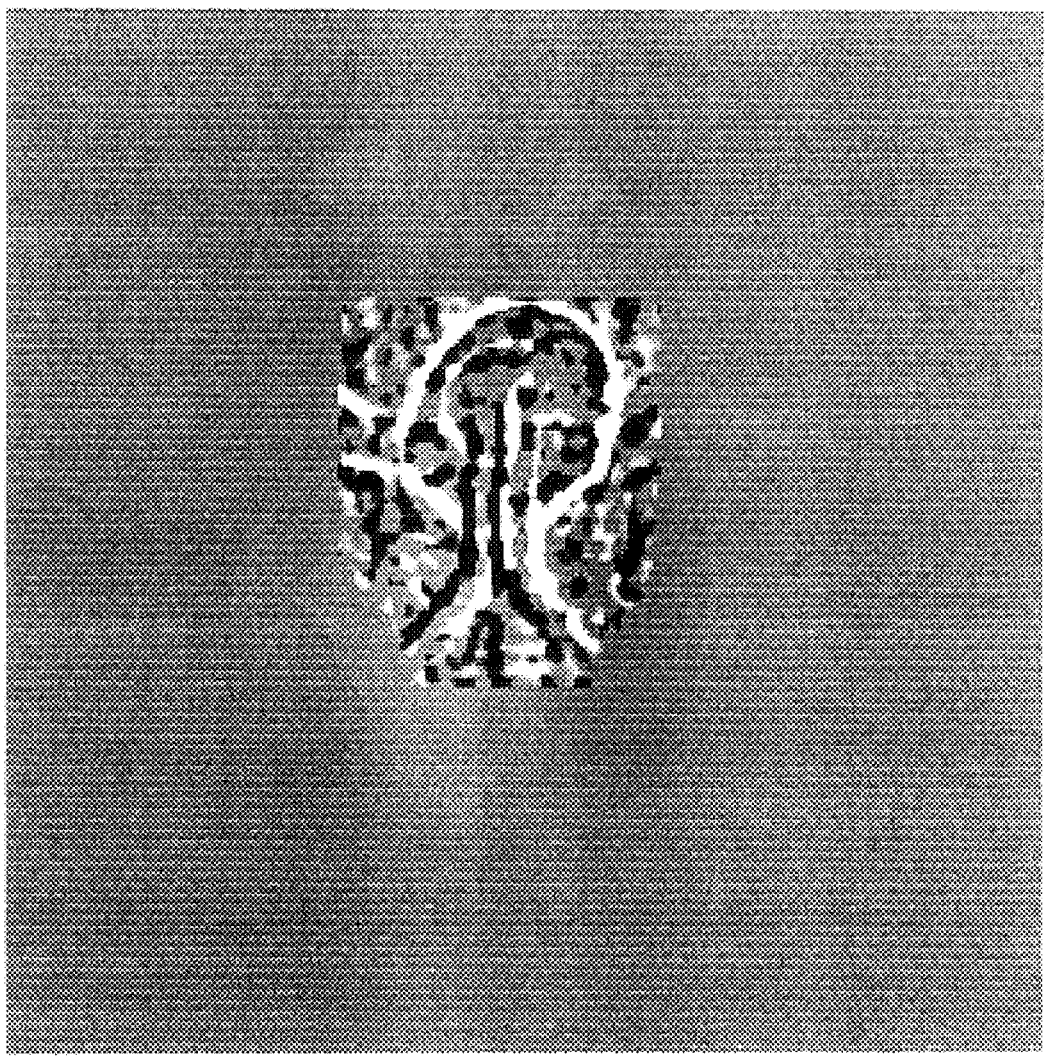
FIG. 12 shows a difference image of two Portal images prior to anatomical registration.
Figure 13:
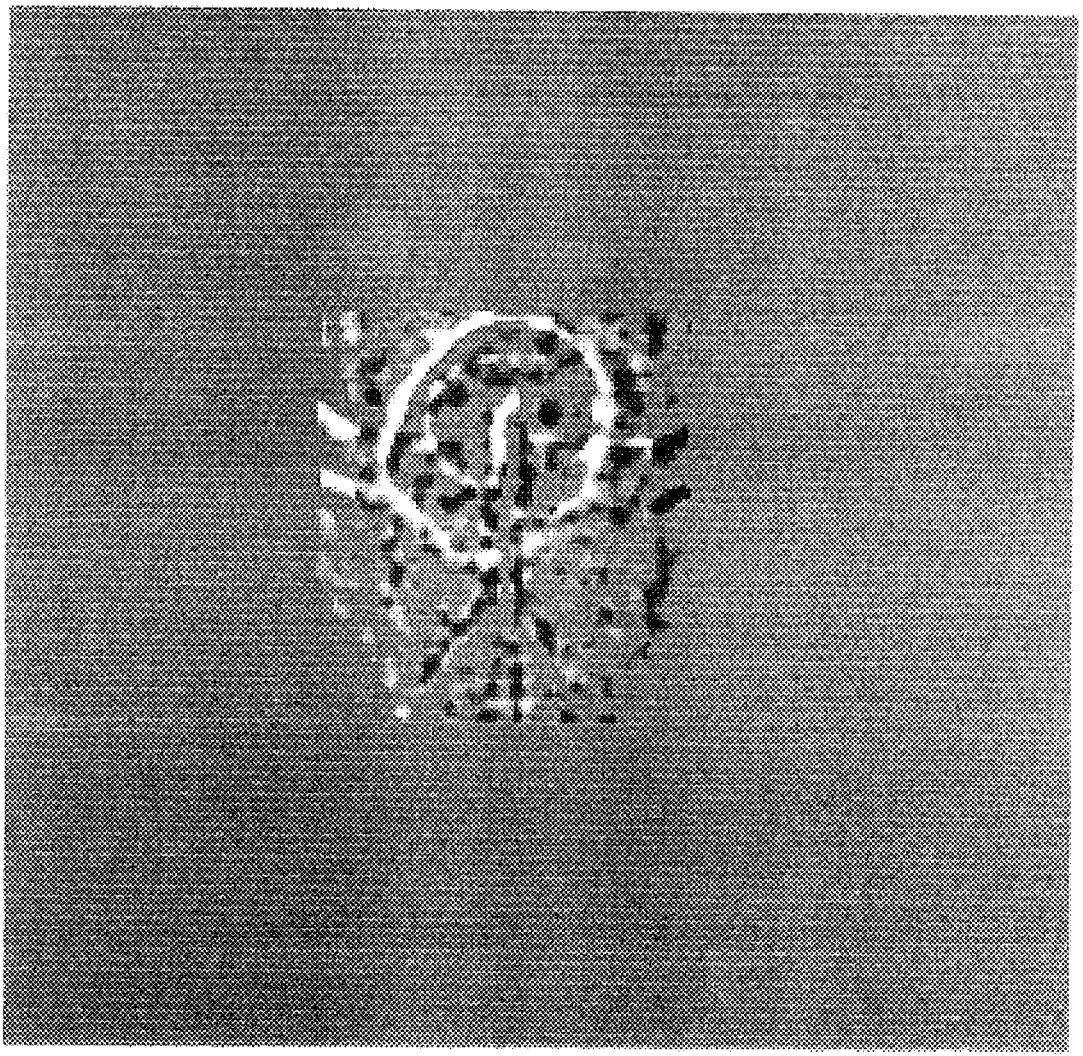
FIG. 13 shows a difference image of two Portal images after anatomical registration.

The success of the matching was controlled visually by creating a difference image of the anatomical structure before and after the matching (FIG. 12, FIG. 13). The bony structures of the Reference Image are white and in the Portal image they are black. A human observer immediately realises when the matching does not perform correctly.

Figure 14:
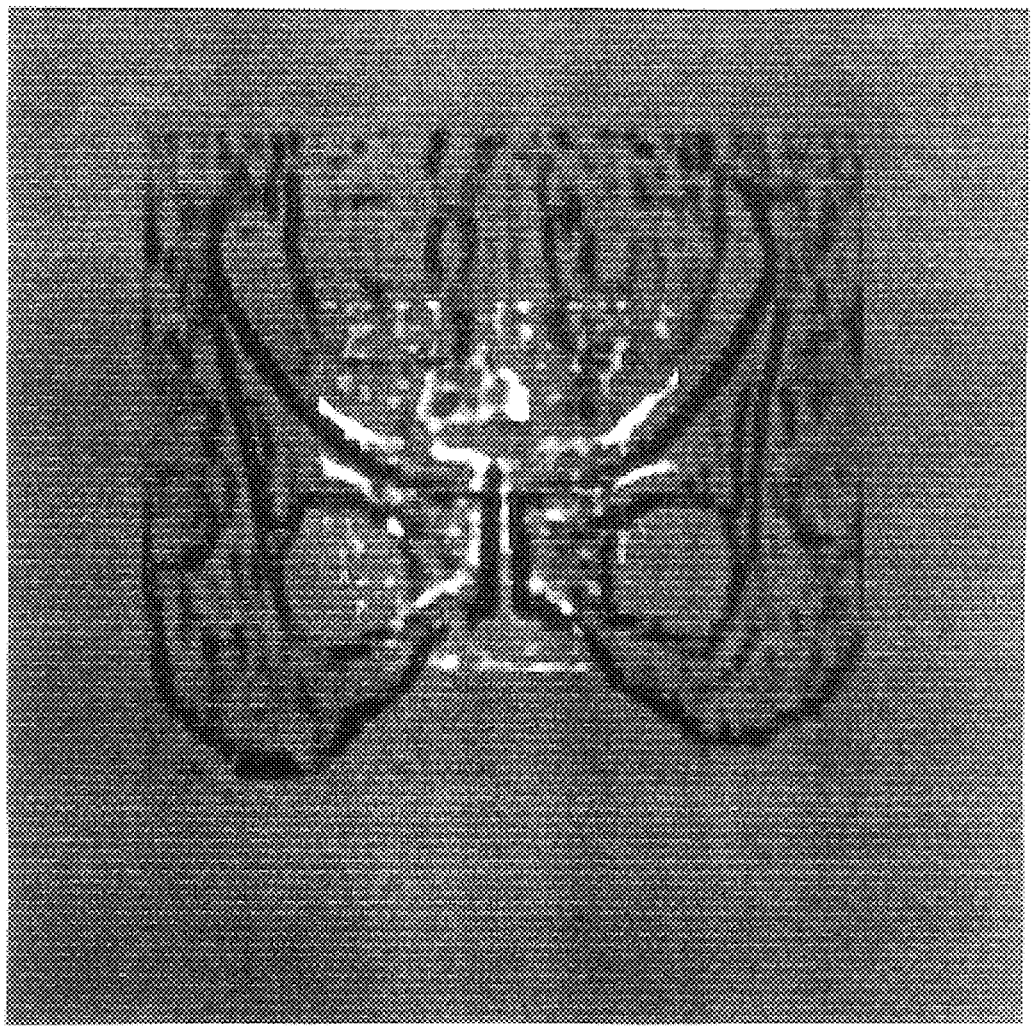
FIG. 14 shows a difference image of a DRR and a Portal image prior to anatomical registration.
Figure 15:
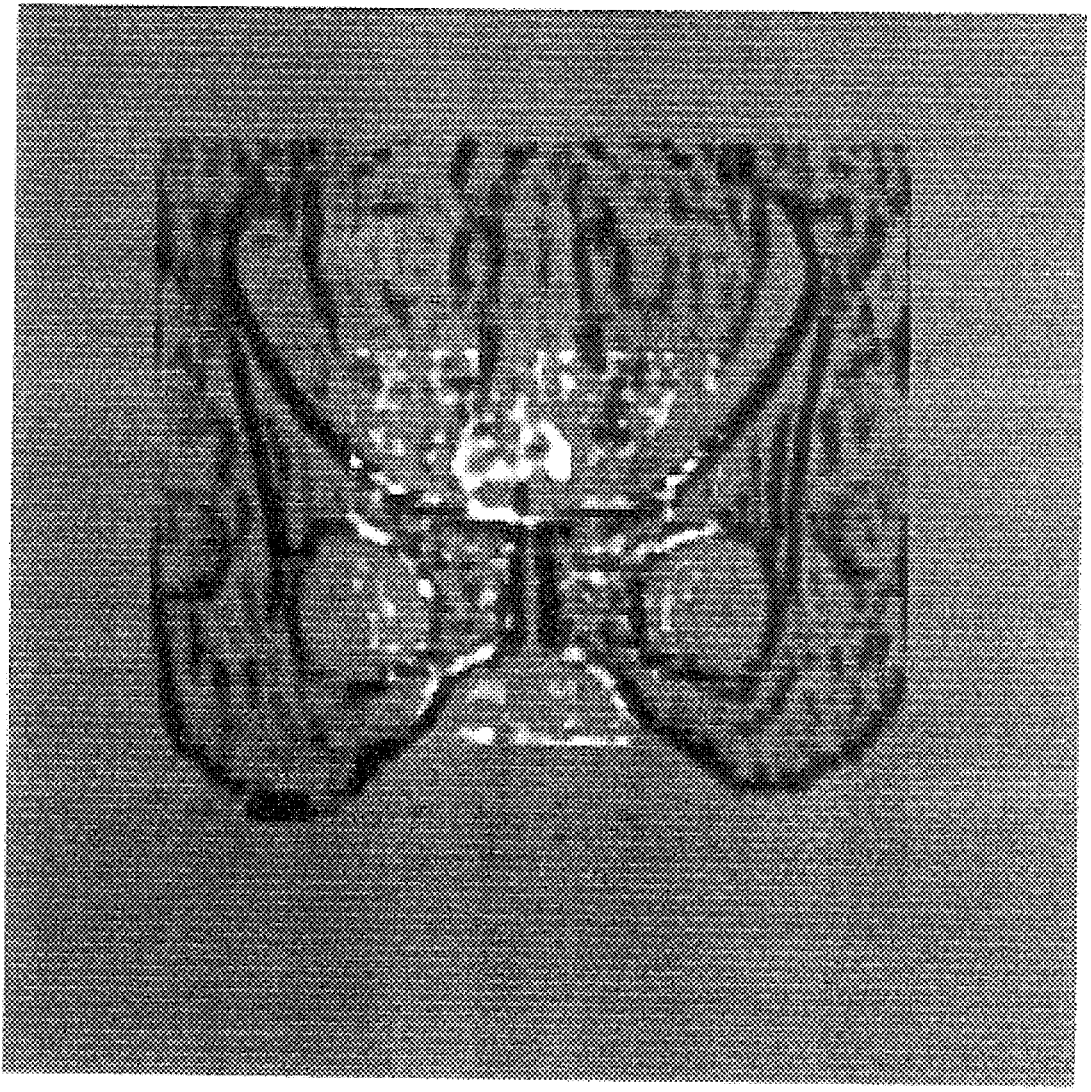
FIG. 15 shows a difference image of a DRR and a Portal image after anatomical registration.

In addition, we examined the matching results when the Reference Image was either a DRR or an image created interactively by drawing lines on top of bony ridges. We tested the matching of such a Reference Image with 17 Portal images from the pelvic region and were in every case successful. This was even the case when the image quality of the Portal image was especially poor or the Portal image contained artifacts like dosimeters. FIG. 14 and FIG. 15 show again two difference images before and after the matching of bony structures where the Reference Image is a highpass filtered DRR.

An average success rate of approximately 98% is very encouraging and shows the superiority of the structure based matching algorithms to grey-level based methods.

There was one sequence of Portal images (lateral images from the pelvis) where the algorithm did not produce reliable results for the shift of the patient. The reason was that the relevant anatomical structures which had to be matched were lying very close to the edge of the radiation filed (the radiation field was rather small). By calculating the Bandpass filtered images and subsequent shrinking of the radiation field (as described above in II.4), the relevant anatomical information was either completely or at least partially removed. As a consequence, even interactively it was difficult to identify the shift of the patient reliably. Therefore, this image sequence was not classed as a failure for the on-line algorithm. It simply emphasises the fact that the user has to examine the Reference Image carefully before the actual treatment starts and make sure that the relevant anatomical structures which should be matched are inside the radiation field. An extreme example would be Portal images where no anatomical structures are present and where the above described algorithm would clearly be unable to calculate meaningful results. In addition, the user has sometimes to choose carefully an appropriate Region of Interest in the Reference Image to suppress disturbing features which should not be matched.

For Portal images of 256×256 pixels the algorithm takes approximately 1.8 seconds on a SPARC-20 workstation which shows that the algorithm can indeed be used for a fast on-line control in the clinical environment.

Modifications to the above process are clearly possible. For example, median filters for the removal of point errors are not necessary as other methods can remove point errors reliably. Equally, segmentation of the radiation field area can be performed via other mathematical methods. Indeed, different methods of matching the radiation field areas can be used whilst still employing the second aspect of the invention as set out initially in this application. Noise suppression is not necessarily carried out by a Gaussian filter, and the block filter is not essential for removal of slowly varying grey-levels. Other high pass filters could conceivably be used. Likewise, the edge of the radiation field can be removed via a variety of methods.

Figure 7:
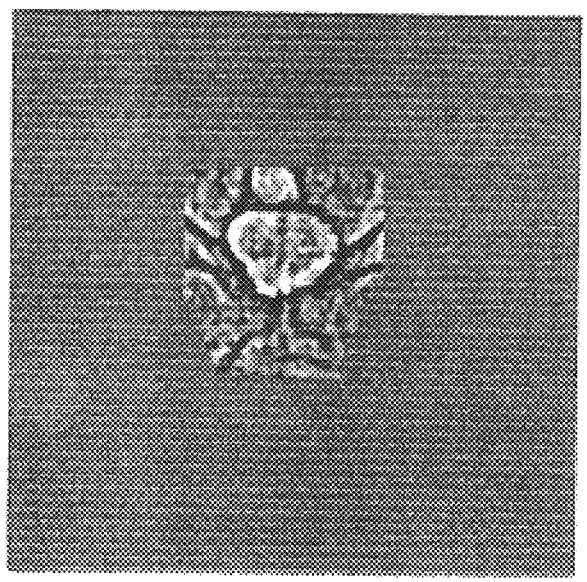
FIG. 7 shows FIG. 5 after removal of the border.

The precise mathematical method for correlating the two structure-based images is equally immaterial to the present invention. The calculation can be done in the spatial domain, in the frequency domain or via a multi-scale method, as can the rotation. The similarity function for calculation of the correlation can be exchanged to alternatives to an NCC. What is important is that the translation and the rotation are determined on the basis of the structure based images, in order to convert the poor correlation of FIG. 6 to the straightforward correlation of FIG. 7.

The order of the above described image processing steps is not mandatory. For example, noise suppression can be combined with determination of the translation in Fourier space. All such variations are naturally intended to be included within the scope of the present invention.

What is claimed is:

1. A method of analysing a radiographic image comprising the following steps;

(a) preparing a reference image, wherein the reference image is one of a portal image from a first treatment, a pre-treatment test image, or a digitally reconstructed radiograph;

(b) preparing a sample image;

(c) preparing a reference radiation field image and a sample radiation field image from the reference image and the sample image respectively by, in order, (i) defining a threshold value and (ii) setting pixels within the respective images to a dark or a bright state if darker or brighter than the threshold value;

(d) optionally, comparing the reference radiation field image and the sample radiation field image to determine at least one of their relative rotation, translation and scaling;

(e) subtracting one of the radiation field images from the other thereby to obtain a difference image;

(f) inspecting the difference image to ascertain changes in the radiation field between preparation of the reference image and the sample image.

2. A method according to claim 1 wherein the threshold value is calculated by determining the pixel grey scale histogram of one or both images and selecting a value between two peaks of the histogram.

3. A method according to claim 2 wherein the value selected is within 10% of the mid-point between the two peaks.

4. A method according to claim 1 wherein the dark state is a zero brightness.

5. A method according to claim 1 wherein the bright state is a maximum brightness.

6. A method according to claim 1 wherein the difference image is inspected by counting the total number of pixels in either the dark or the bright state and determining whether the count is above or below a preset figure.

7. A method according to claim 6 wherein an alarm is generated if inspection shows a significant difference between the images.

8. A method according to claim 1 wherein the sample image is a Portal image taken during a radiotherapy treatment.

9. A method according to claim 1 wherein the sample image is captured electronically and analysed during the therapeutic radiotherapy treatment.

10. A method according to claim 9 wherein data is captured during the first 10 seconds.

11. A method according to claim 9 wherein data is captured during the first 5 seconds.

12. A method according to claim 9 wherein the radiotherapy session is automatically ended if inspection reveals a significant error.

13. A radiotherapy treatment apparatus comprising:
(a) means for digitally capturing a Portal image and
(b) means for analysis of that image;
the analysis means being adapted to operate as set out in claim 1.

14. A method of treating a patient by radiotherapy, comprising the steps of placing the patient in range of a radiation source, activating the source, capturing a sample Portal image and analysing the sample image according the image analysis method set out in claim 1, and de-activating the radiation source if analysis shows a significant difference between the images.

15. A method of analysing a radiographic image comprising the following steps:
(a) preparing a reference image, wherein the reference image is one of a portal image from a first treatment, a pre-treatment test image, or a digitally reconstructed radiograph;
(b) preparing a sample image;
(c) filtering at least the sample image to remove low frequency variations;
(d) selecting a region of interest (ROI) within the reference and sample images;
(e) correlating the ROI of the reference image with the ROI of the sample image;
(f) determining the relative displacements of the reference image and the sample image.

16. A method according to claim 15 wherein the region of interest (ROI) is a selected field of the image.

17. A radiotherapy treatment apparatus comprising:
(a) means for digitally capturing a Portal image and
(b) means for analysis of that image;
the analysis means being adapted to operate as set out in claim 15.

18. A method of treating a patient by radiotherapy, comprising the steps of placing the patient in range of a radiation source, activating the source, capturing a sample Portal image and analysing the sample image according the image analysis method set out in claim 15, and de-activating the radiation source if analysis shows a significant difference between the images.

19. A method of analysing a radiographic image comprising the following steps:
(a) preparing a reference image;
(b) preparing a sample image comprising the steps of:
preparing a preliminary sample image;
preparing a reference radiation field image and a preliminary sample radiation field image from the reference image and the preliminary sample images respectively by, in order, (i) defining a threshold value and (ii) setting pixels within the respective images to a dark or a bright state if darker or brighter than the threshold value; and
subtracting one of the radiation field images from the other thereby to obtain the sample image;
(c) filtering at least the sample image to remove low frequency variations;
(d) selecting a region of interest (ROI) within the reference and sample images;
(e) correlating the ROI of the reference image with the ROI of the sample image;
(f) determining the relative displacements of the reference image and the sample image.

20. A method according to claim 19 in which the sample image is shrunken prior to processing.

21. A method according to claim 20 wherein the shrinking step is carried out by setting each pixel to a dark state unless all four neighbours are bright.

22. A method according to claim 20 in which the sample image is shrunken by more than one pixel.

23. A method according to claim 22 in which the shrinking step is carried out by setting each pixel to a dark state unless all four neighbours are bright, the neighbours being those pixels separated from the pixel concerned by a preset distance.

24. A method according to claim 23 wherein the distance is between 15 and 30 pixels.

25. A method of analysing a radiographic image comprising the following steps:
(a) preparing a reference image;
(b) preparing a sample image, the sample image being a Portal image taken during a radiotherapy treatment;
(c) filtering at least the sample image to remove low frequency variations;
(d) selecting a region of interest (ROI) within the reference and sample images;

(e) correlating the ROI of the reference image with the ROI of the sample image;

(f) determining the relative displacements of the reference image and the sample image.

26. A method of analysing a radiographic image comprising the following steps:

(a) preparing a reference image;

(b) preparing a sample image, wherein the sample image is captured electronically and analyzed during therapeutic radiotherapy treatment;

(c) filtering at least the sample image to remove low frequency variations;

(d) selecting a region of interest (ROI) within the reference and sample images;

(e) correlating the ROI of the reference image with the ROI of the sample image;

(f) determining the relative displacements of the reference image and the sample image.

27. A method according to claim 26 wherein data is captured during the first 10 seconds.

28. A method according to claim 26 wherein data is captured during the first 5 seconds.

29. A method according to claim 26 wherein the radiotherapy session is automatically ended if inspection reveals a significant error.

* * * * *